United States Patent [19]

Iwatschenko et al.

[11] Patent Number: 4,625,494
[45] Date of Patent: Dec. 2, 1986

[54] METHOD AND APPARATUS FOR MAKING MIXTURES OF PHARMACEUTICAL LIQUIDS

[75] Inventors: Peter Iwatschenko, Neunkirchen; Fritz Giebler, Meitingen-Ostendorf, both of Fed. Rep. of Germany

[73] Assignee: Pfrimmer & Co. Pharmazeutische Werke Erlangen, Erlangen, Fed. Rep. of Germany

[21] Appl. No.: 808,668

[22] Filed: Dec. 13, 1985

Related U.S. Application Data

[63] Continuation of Ser. No. 489,645, Apr. 28, 1983, abandoned.

[51] Int. Cl.[4] .............................................. B65B 31/02
[52] U.S. Cl. .................................... 53/432; 53/510; 604/82
[58] Field of Search ............... 53/86, 237, 434, 469, 53/474, 502, 512; 137/154, 205; 141/83, 94, 96, 100, 104, 105, 114, 315, 317; 604/80–83, 122, 245

[56] References Cited

U.S. PATENT DOCUMENTS

| 2,035,252 | 5/1958 | Mauchel | 604/122 |
| 2,928,216 | 3/1960 | Orsini | 53/469 X |
| 3,875,980 | 4/1975 | Getz | 141/83 |
| 3,878,907 | 4/1975 | Morick | 141/83 X |
| 3,965,646 | 6/1975 | Hawkins | 53/512 |
| 4,094,318 | 6/1978 | Burke et al. | 604/245 X |
| 4,111,335 | 9/1978 | Arya et al. | 141/105 X |
| 4,258,712 | 3/1981 | Harms et al. | 604/122 X |
| 4,267,837 | 5/1981 | Purdy et al. | 604/245 X |
| 4,372,100 | 2/1983 | Miller et al. | 53/512 X |

FOREIGN PATENT DOCUMENTS

| 2601432 | 7/1977 | Fed. Rep. of Germany | 604/122 |
| 604741 | 9/1978 | Switzerland | 604/122 |

Primary Examiner—John Sipos
Assistant Examiner—Steven P. Weihrouch
Attorney, Agent, or Firm—Jordan and Hamburg

[57] ABSTRACT

Method for the preparation of mixtures of pharmaceutical liquids, for example infusion solutions, from storage containers containing at least two of the individual mixture components, in an arrangement with a vacuum chamber to receive the containers to be filled and with a connecting hose for each storage container as well as a tube connected to the container to be filled and also connected with the connection hoses of the storage containers via a hose connection, with the attainment of the desired predetermined amount of each mixture component being indicated by registering air intake into the individual connection hoses, clamping the respective connecting tube and sealing and cutting the hose downstream from the clamping following corresponding registration of air intake into all present connection hoses.

21 Claims, 5 Drawing Figures

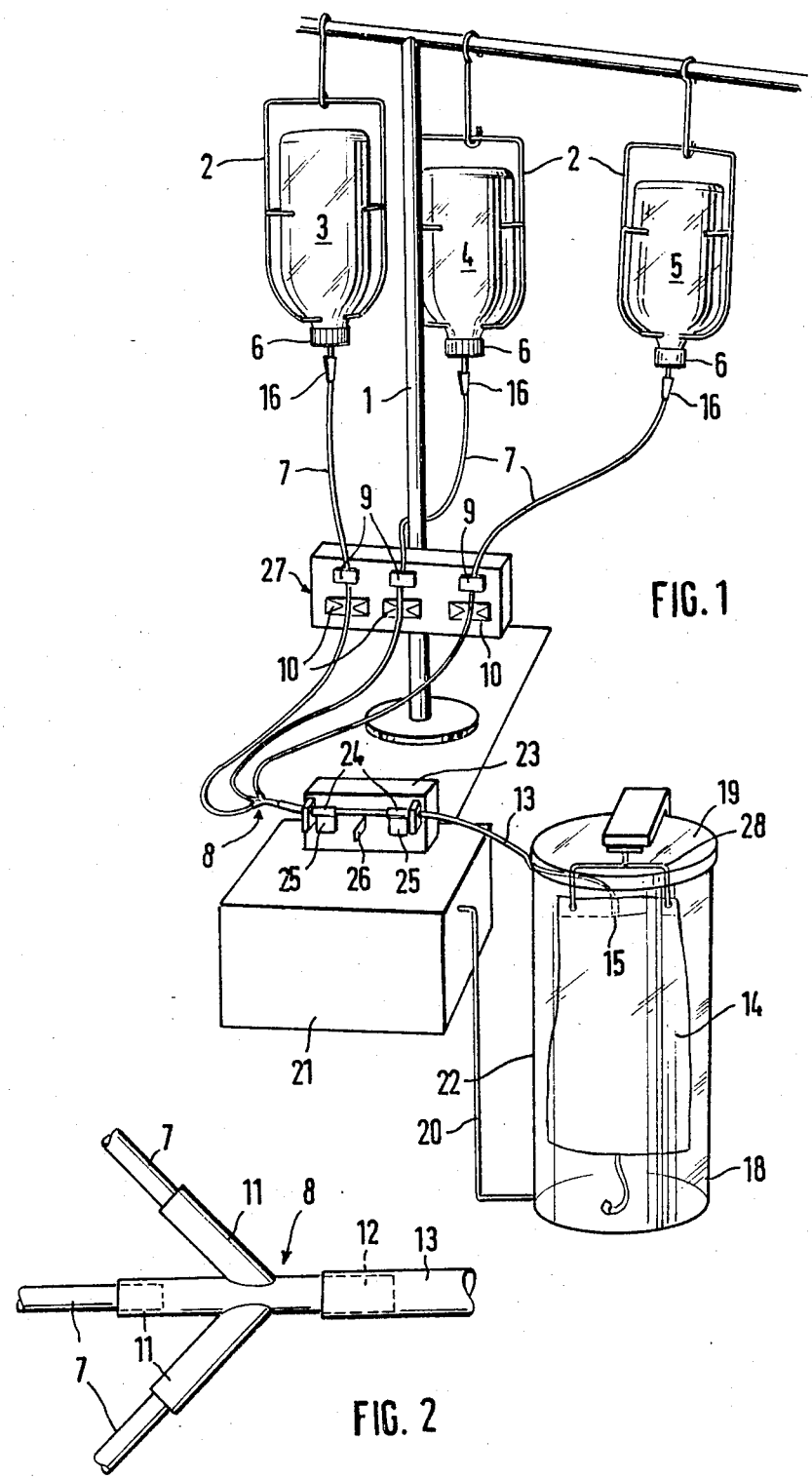

METHOD AND APPARATUS FOR MAKING MIXTURES OF PHARMACEUTICAL LIQUIDS

This application is a continuation of application Ser. No. 489,645, filed Apr. 28, 1983, now abandoned.

BACKGROUND OF THE INVENTION

The invention relates to a method and an apparatus for the preparation of mixtures of pharmaceutical liquids, for example, infusion solutions, with storage containers containing at least two of the individual mixture components, a vacuum chamber to receive the container to be filled, and with a connecting hose for each storage container as well as a hose connected to the container and connected through a hose connection to the connecting tube of the storage container to be filled.

Preparations comprising several different components have to be mixed for the most diverse fields of application in medicine, especially for parenteral feeding in which the individual components often cannot be sterilized or prepared or stored together. For medical as well as practical reasons, a mixed administration is, however, still preferred. In many instances, it is therefore necessary to prepare the mixture in an additional container which actually means preparing a brand new medicine by the hands of a physician or pharmacist. When these mixtures are frequently used, it is often desirable to have them available in storage. It is obvious that this preparation of mixed solutions, such as, for example, mixed infusion solutions, generally penetrates the sealed system of the storage containers, which is most undesirable. The object is therefore to accomplish a virtually contamination-free preparation of such mixtures, i.e. a preparation without manual manipulation, with the individual components of the mixture having a predetermined proportion to one another.

The state of the art provides for the filling of sterile bag-like containers by pumping in the individual components. The filing amount is determined by the reference output volume of the pump. Additionally, the total mixture is weighed. In addition to the fact that such mixture preparation and filling methods do not meet present demands for rapid processing, the known arrangements are not sealed systems, and thus are not contamination-free. Furthermore, there is the danger of particles rubbing off from the pump hose. Finally, the dosage system of this apparatus regarding the individual components is not sufficiently reliable, depending solely on the total weight of the mixture. Thus, the individual components might not have the desired proportion to one another.

There is therefore an urgent need for an arrangement which allows extremely rapid filling of containers with a mixture of pharmaceutical liquids, precisely adhering to the predetermined amounts of the individual components, and being contamination-free in a virtually sealed system. By avoiding any handling of the arrangement and the containers during filling, it is possible to prepare such special pharmaceutical liquid mixtures to be used according to medical prescription, and to keep them stored by pharmacists, not by the manufacturers. The air inherent in the system and present, for example, in the racking hose, can be ignored.

SUMMARY OF THE INVENTION

The object of the invention is accomplished by an arrangement of the initially described type with each of the connection hoses that are connected to a storage container being guided through a sensor for indicating the air content in the respective hose, and subsequently through a clamping device connected to the sensor, with the tube connected to the container to be filled being guided through a sealing device having two sealing points at a distance from one another, as well as having an intermediate cutting device, the sealing device being connected with the clamping device.

The container, maintained under external vacuum, is connected to the storage containers holding the individual components of the mixture to be prepared through a tube, hose connection and connecting hoses. Because of the vacuum effect, all mixture components can be transferred to the container at the same time. If a storage container is empty and if the connecting hose leading to the hose connection is subsequently filled with air, then this condition is immediately registered by the corresponding, preferably optically acting sensor, and the concomitantly released signal is transferred to the corresponding clamping device. This effects the immediate clamping of the respective hose. The vacuum acting in the vacuum chamber, and transferred to the container to be filled, ceases to act on the corresponding storage container, while the emptying of the additional storage containers containing the other mixture components continues. The described process (i.e. that the sensor arranged with each connecting hose clamps the respective hose when the corresponding storage container is empty and air appears in the hose) continues until the last sensor has been activated. This then activates the downstream sealing device, which mechanically, or depending on the substance, seals the tube leading to the container to be filled in two places at a distance from one another. At the same time, the tube is cut between the two sealing points. It is useful if this arrangement is turned off at the same time. Having removed the negative pressure in the chamber, it can be opened and the filled container removed. The entire process takes less than two minutes, and is thus essentially faster than any arrangement heretofore known in the state of the art.

It is within the scope of the invention according to the basic principle, to provide the hose connection at the sides facing the container to be filled, with two or more hose connections for the connection of several hoses, each of which is connected to a container. In this specific embodiment, the hose connection is not only connected to two or more storage containers (which would mean that the mixture can comprise two or more individual components), but it can at the same time be connected to more than one container to be filled. Clearly, several containers can be brought to the vacuum chamber at the same time in this embodiment and thus be filled at the same time. It is, on the other hand, in the case of correspondingly smaller vacuum chambers, also possible to bring only one container (i.e. one bag or the like) of all bags connected to the hose connection to the vacuum chamber for filling, while the other bags connected with the hose connection remain outside the vacuum chamber. A positive differential pressure acts on the container to be filled, while a negative differential pressure acts on the containers to be filled located outside the chamber. The difference between the two pressures results in only the container located in the vacuum chamber being filled. The desired sealed system for contamination-free filling of pharmaceutical mixtures is maintained in this embodiment as well. The individual bags connected to the system can successively be brought into the chamber and filled.

It has been shown to be disadvantageous if there is an unnecessarily large distance between the sealing device and the bags located in the vacuum chamber. The filling tube, remaining on the container, being sealed at its free end, is often viewed as disturbing in later use. The invention therefore provides for the sealing device to be located inside the vacuum chamber. This results in an extremely short tube length between the sealing device and the bag to be filled. The sealing device can also be arranged on the bottom side of the cover of the vacuum chamber or on the inside of the chamber wall, in any event at a location where the distance to the bag in the chamber is minimal.

The invention is based on the mixture proportions being determined by correspondingly measuring volume in the storage containers. However, it is also possible to determine the respective weight of the mixture proportions with the total amount being the amount of the total mixture measured according to the weight. In order to accomplish this, another feature of the invention provides for a scale inside the vacuum chamber, with the container attached to the scale in freely movable fashion, and with the scale and the sealing device, whether arranged inside or outside the vacuum chamber, connected to a control device serving to preprogram the weight of the individual mixture components. In this embodiment, the functional process comprises the individual mixture components being filled in the containers in chronological succession. If the requisite amount of the first mixture portion has been filled into the container, the scale releases a signal which activates the clamping device. When the desired filling level has been reached, the sealing of the connecting hose is also effected, with an amount of liquid still present in the respective storage container. At the same time, the signal released from the scale opens the previously-closed clamping device of the subsequent storage container and its mixture components now flow into the container to be filled. The described process is repeated until the last storage container, with the last mixture component, has been reached. The guidance of the scale is programmed so that the weights of the individual components of the mixtures are added to one another.

If the last storage container has supplied the desired and intended amount of liquid for the mixture to be prepared, the clamping device is closed and the sealing device, as in the above embodiment, is directed to sealing the tube leading to the container to be filled as well as to the cutting device. After having opened the vacuum chamber, the filled container can be removed and labeled. Thereafter, the next bag can be brought into the chamber and filled without renewed connection of a new container and the concommitantly-related risk of contamination.

The sealing device of the arrangement according to the invention is especially dependable, and the arrangement can be correspondingly simplified when, as the invention further provides, two operable metal sleeves are pushed onto the tube connected to the container to be filled, at a distance from one another corresponding to the distance of the sealing position of the sealing device with the tube having the metal sleeves then being inserted into the sealing device. The tube can thus be clamped easily and reliably in a mechanical fashion by clamping the sleeves. Of course, welding the tube represents an alternative.

Additional characteristics, details and advantages of the invention can be observed in the following description of a few preferred embodiments, as well as from the drawings.

BRIEF DESCRIPTION OF THE DRAWINGS

In the drawings:

FIG. 1 is a first embodiment in schematic representation,

FIG. 2 is an enlarged detail of this embodiment.

DETAILED DESCRIPTION OF THE PREFERRED EMBODIMENTS

Figure 3:
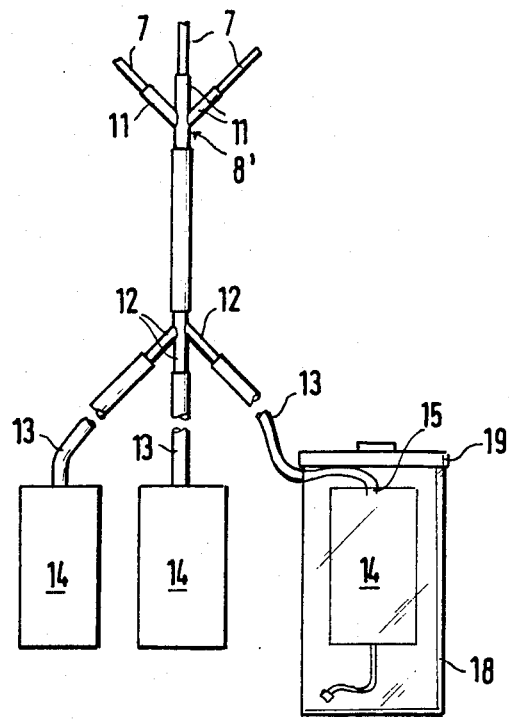
FIG. 3 is a varied embodiment in broken representation.

In the illustrated embodiment, three storage containers 3, 4 and 5 in their emptying position, i.e. with sealed opening 6 pointing downwardly, have been hung on a stand 1 or other frame in corresponding holders 2. A connection hose 7 of suitable cross-section is connected to each of the container seals 6. In general, these hoses are made of PVC. These connection hoses 7 are guided past a sensor 9 which addresses the air contained in the hoses 7 in the direction of a hose connection 8. Sensors 9 can, for example, function optically. A clamping device 10 is connected to each sensor 9, which operates magnetically, for example, and, if released by a signal from sensor 9, clamps the respective connecting hose 7, preventing a continued conveyance from the respective storage containers 3, 4, 5.

Hose conection 8 has connection pieces 11, corresponding to the number of connection hoses 7, tightly connecting the hoses 7. In the embodiment in FIGS. 1 and 2, a single downstream connection piece 12 is provided, which is furthermore tightly connected to the tube 13, leading to the container to be filled, i.e. bag 14. Tube 13 terminates at 15 at the head of the bag 14. Container 14 as well as the hose system comprising tube 13 and connecting hoses 7, hose connection 8 and connection cannulas 16, form a unit which is produced and packaged in sterile fashion and not removed from the packaging (not illustrated) until ready to use, i.e. for the filling of container 14.

The arrangement furthermore comprises a vacuum chamber 18 which is sealed by a hinged cover 19 and is connected to the vacuum generator 21 via conduit 20 (not illustrated in detail). In the upper area of wall 22, an airtight inlet for the tube 13 leading to container 14 is provided. The vacuum generator 21 has a sealing device 23 through which hose 13 is led. Two slightly movable sleeves 24 are pushed onto tube 13 in a tightly fitting fashion. As can be sen from FIG. 1, these are located in the sealing device 23 in the area of the two sealing points 25 which have corresponding utensils for the deformation of sleeves 24 and thus for the sealing of tube 13. Between the two sealing points 25, a cutting knife 26 of a cutting device has been arranged in order to separate tube 13 between the two sealing points 24.

The embodiment according to FIGS. 1 and 2 operates as follows:

The containers 3, 4 and 5 hanging on stand 1 contain the necessary equal or differing amounts of the various mixture components for the pharmaceutical mixture to be prepared. Cannulas 16 of connecting hoses 7 are connected to container seals 6 and to the hoses placed into unit 27 which comprises sensors 9 and clamping devices 10 and can also be attached to the stand 1. Then, tube 13 arranged downstream from hose connection 8 is placed into the sealing device 23 and the bag 14, arranged at the end of tube 13, is hung onto a hanger 28 on the inside of cover 19 of vacuum chamber 18. By using the vacuum generator 21, the chamber 18 is placed under negative pressure, and upon open clamping devices 10, the contents of storage containers 3, 4 and 5 flow through the hose system into the containers 14 to be filled (PVC bags). If the storage containers 3, 4 and 5 contain differing amounts, the corresponding sensor 9 of the connection hose 7 of the storage containers 3, 4 and 5 having the smallest filling amount registers air filling first. This immediately releases a signal, closing the corresponding clamping device 10, which can be operated, magnetically, for example. Thus, this hose is blocked and no air can enter into container 14. This process is repeated with the remaining storage containers. When the last sensor 9 registers, all clamping devices 10 are closed, and sealing device 23 is released, the sealing points 25 of which seal tube 13, leading to container 14, at two points at a distance from one another. Then, the cutting device 26 cuts the piece of hose situated between the two sealing points. At the same time, the vacuum generator 21 is turned off and vacuum chamber 18 ventilated so that cover 19 can be opened and container 14 located therein removed, labeled and transferred for further treatment.

The embodiment according to FIG. 3 differs from the one just described in that the hose connection 8' has more than one connecting tube on the downstream side. Three connection pieces 12 in the illustrated embodiment are each connected to a tube 13 leading to a container 14. Two or more than three such connection pieces 12 can be provided on hose connection 8. The same applies to connection pieces 11 leading to the storage containers 3, 4 and 5.

In this embodiment, a container 14 to be filled is received in vacuum chamber 18 and filled in the manner described above, while the other bags 14 remain outside the vacuum chamber. Due to the various differential pressures, containers 14 outside the vacuum chamber 18 remain unfilled, and the liquid only fills container 14 inside the vacuum chamber 18. In this manner, a number of containers 14 can be successively filled, presuming correspondingly large storage containers 3, 4 and 5 or smaller filling volumes of containers 14, suitable for example for pediatric purposes.

Figure 4:
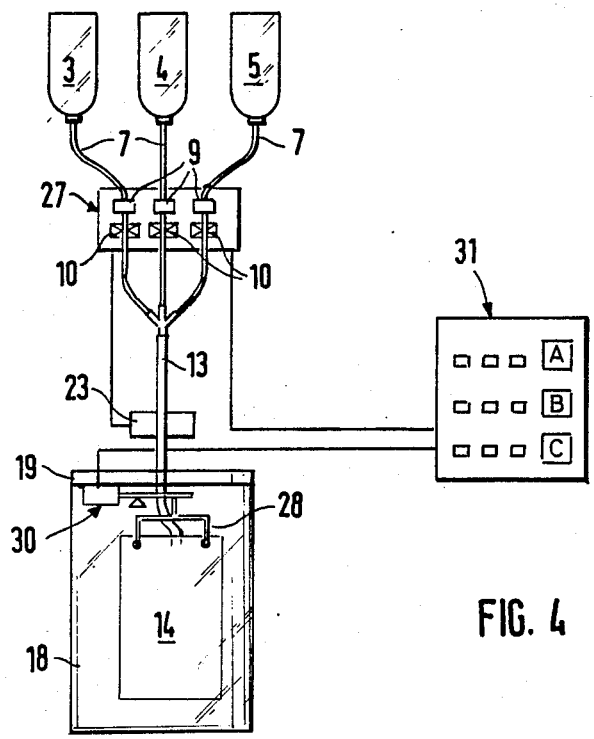
FIG. 4 is an additional embodiment.

FIG. 4 illustrates an embodiment with an electronic scale 30 inside the vacuum chamber 18. It is mounted on the inside of cover 19 (which seals chamber 18) and has a hanger 28 to receive container 14 to be filled, which hangs freely in the vacuum chamber 18. Scale 30 is connected to a control device 31 in which the filling systems, corresponding to the programming of the mixture components in the storage containers 3, 4 and 5 are respectively labeled A, B and C. The control unit 31 is additionally connected to unit 27 which comprises sensors 9 and clamping devices 10. In this embodiment, which naturally also can be designed as described in FIG. 3, the determination of the component proportions forming the basis of the mixture to be prepared is made according to weight. For this purpose, all clamping devices 10 are closed at the beginning of the filling process. They are opened, one by one, in order to fill the preprogrammed amount determined by control device 31. As soon as this filling of container 14 has been accomplished, as indicated by scale 30, control device 31 is given a corresponding signal. This in turn addresses unit 27. Thus, the previously-opened clamping device 10 is closed and the subsequent one is opened so that the next mixture component can flow into container 14. The weight of the first mixture component is added to the desired weight proportion of the second component in control device 31. If this weight is reached by the corresponding filling of container 14, and indicated by the electronic scale, control device 31 is again addressed and from here, unit 27 or its clamping devices 10. This process continues until all mixture parts have been filled up to the desired amounts. If a storage container 3, 4 or 5 is emptied so that air gets into the connecting hose 7, the corresponding sensor 9 would register and close the connecting hose 7.

Figure 5:
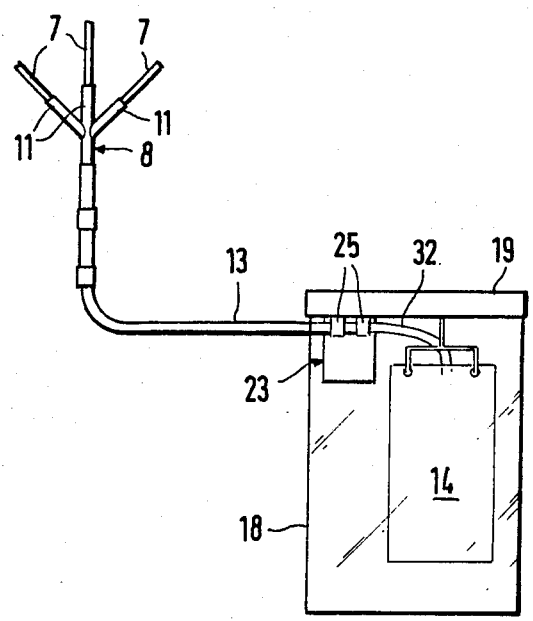
FIG. 5 is an additional variation of the invention, in schematic representation as well.

The embodiment according to FIG. 5 is characterized by the sealing device 23 being arranged inside the vacuum chamber 18. This results in a very short end 32 of tube 13 remaining on the bag 14 after cutting tube 13 between the two sealing points 25. This remaining end is no longer disturbing when using container 14 later on. Additionally, the sealing device 23 may have a pneumatic or hydraulic drive.

We claim:

1. Apparatus for the automatic preparation and accurate mixing of predetermined amounts of pharmaceutical liquid contamination-free in a closed system, comprising a plurality of closed supply containers containing the liquid components to be mixed, a supply tube leading from each of said containers, a cannula connecting each respective supply container and supply tube, a connector means having a plurality of connector inlets and a connector outlet with each of said connector inlets being in communication with said connector outlet, each of said supply tubes being connected to one of said connector inlets of said connector means, a sensor means in each of said supply tubes located between said supply container and said connector means, said sensor means including means to sense emptying of the respective supply container by sensing air in the respective supply tube, closure means in each of said supply tubes located between said sensor means and said connector means and operable to close off the respective supply tube when said sensor means senses emptying of the respective supply container, a vacuum chamber, a receptacle to be filled with the mixed pharmaceutical liquid, said receptacle being disposed within said vacuum chamber, a conduit leading from said outlet connection of said connector means and passing sealingly into said vacuum chamber for connection to said receptacle, said cannulas, said supply tubes, said connector means, said conduit, and said receptacle being formed as a single connected unit which is packaged in a sterile condition, a sealing means located along said conduit downstream of said closure means and said connector means to seal said conduit after said receptacle receives the pharmaceutical liquid from said supply containers, whereby the apparatus is operable to pass the liquid simultaneously from all of said closed supply containers to said receptacle in said vacuum chamber along a sealed flow path sealed from the outside atmosphere while air is prevented from entering said receptacle upon emptying of the respective supply container by the sensor means which operates the respective closure means to close off the respective supply tube when air is present in the respective supply tube upon emptying of the respective supply container, the apparatus thereby providing for automatic and exact filling of the receptacle under sterile conditions.

2. Apparatus according to claim 1, wherein said sealing means comprises two sealing elements spaced from one another and operable to seal said conduit at two spaced locations, and cutting means located in said space between said two sealing elements for cutting said conduit between said two spaced locations.

3. Apparatus according to claim 2, wherein said sealing means comprises two metal sleeves, each situated around said conduit at said respective spaced locations.

4. Apparatus according to claim 2, wherein said sealing means is pneumatically actuated.

5. Apparatus according to claim 2, wherein said sealing means is hydraulicallly actuated.

6. Apparatus according to claim 1, wherein said sealing means is disposed outside said vacuum chamber.

7. Apparatus according to claim 1, wherein said sealing means is disposed inside said vacuum chamber.

8. Apparatus according to claim 1, wherein said closure means is magnetically actuated.

9. Apparatus for the automatic preparation and accurate mixing of predetermined amounts of pharmaceutical liquids contamination-free in a closed system, comprising a plurality of closed supply containers containing the liquid components to be mixed, a supply tube leading from each of said containers, a connector means having a plurality of connector inlets and a plurality of connector outlets with each of said connector inlets being in communication with each of said connector outlets, each of said supply tubes being connected to one of said connector inlets of said connector means, a sensor means in each of said supply tubes located between said supply container and said connector means, said sensor means including means to sense emptying of the respective supply container by sensing air in the respective supply tube, closure means in each of said supply tubes located between said sensor means and said connector means and operable to close off the respective supply tube when said sensor means senses emptying of the respective supply container, a vacuum chamber, a plurality of receptacles to be filled with the mixed pharmaceutical liquid, one of said receptacles being disposed within said vacuum chamber, a conduit connected to each of said connector outlets of said connector means and connected to each of said respective receptacles, one of said conduits connected to said one receptacle passing sealingly into said vacuum chamber, a scale means operable to weigh said one receptacle, a control means connected between said scale means and said closure means and operable to selectively open and close said closure means to effect sequential flow of predetermined amounts and weights of liquid from each of said supply containers into said one receptacle, and a sealing means located along said one conduit downstream of said closure means and said connector means to seal said one conduit after said one receptacle receives said predetermined amounts and weights of pharmaceutical liquids from said supply containers, whereby the apparatus is operable to sequentially pass predetermined amounts and weights of the pharmaceutical liquids from said supply containers to said one receptacle in said vacuum chamber in a flow path closed from the surrounding atmosphere, the apparatus also being operable to prevent air from entering said one receptacle upon eventual emptying of the respective supply container by the sensor means which operates the respective closure means to close off the respective supply tube when air is present in the respective supply tube upon emptying of the respective supply container, the apparatus thereby providing for automatic and exact filling of receptacles under sterile conditions, said one receptacle, upon receiving said predetermined amount of weights of pharmaceutical liquids and being sealed, being removed from said vacuum chamber and another of said receptacles connected to another of said conduits being placed into said vacuum chamber to receive predetermined amounts of weights of pharmaceutical liquids from said supply containers along a flow path which is closed and which was closed when said one receptacle was receiving said pharmaceutical liquids, whereby sterile conditions are maintained during filling of said plurality of receptacles, said other receptacle being precluded from receiving pharmaceutical liquids from said supply containers during filling of said one receptacle due to the differential pressure about said one and said other receptacle during filling of said one receptacle.

10. Apparatus according to claim 9, wherein said sealing means comprises two sealing elements spaced from one another and operable to seal said conduit at two spaced locations, and cutting means located in said space between said two sealing elements for cutting said conduit between said two spaced locations.

11. Apparatus according to claim 9, wherein said scale means is disposed in said vacuum chamber.

12. Apparatus according to claim 10, wherein said sealing means comprises two metal sleeves, each situated around said conduit at said respective spaced locations.

13. Apparatus according to claim 10, wherein said sealing means is pneumatically actuated.

14. Apparatus according to claim 9, wherein said sealing means is hydraulically actuated.

15. Apparatus according to claim 9, wherein said sealing means is disposed outside said vacuum chamber.

16. Apparatus according to claim 9, wherein said sealing means is disposed inside said vacuum chamber.

17. Apparatus according to claim 9, wherein said closure means comprises a magnetically actuated drive.

18. A method for automatically preparing and accurately mixing predetermined amounts of pharmaceutical liquids under sterile conditions, comprising the steps of passing the liquid to be mixed from separate closed supply containers along separate supply paths, combining said separate supply paths into a combined flow path leading to the receptacle to be filled with the pharmaceutical liquids, maintaining the outside of said receptacle under vacuum conditions, maintaining said separate supply paths and said combined flow path closed from the surrounding atmosphere, sensing the emptying of each of said supply containers by sensing means which sense the air in the respective separate supply path, closing off the respective supply path by closure means upon sensing said air to thereby prevent air from entering the supply path downstream of said closure means upon emptying of the respective supply container, and thereafter sealing off the contents of said receptacle, whereby the receptacle thereby receives a predetermined amount of pharmaceutical liquid from each of said supply containers along a flow path closed from the surrounding atmosphere and air is prevented from entering said receptacle upon emptying of the respective supply container, thereby providing for automatic and exact filling of the receptacle under sterile conditions.

19. A method for automatically preparing and accurately mixing predetermined amounts of pharmaceutical liquids under sterile conditions, comprising the steps of establishing separate supply paths for the liquid to be mixed, each of said supply paths leading from a separate closed supply container, combining said separate supply paths into a combined flow path leading to the receptacle to be filled with the liquids, maintaining the outside of said receptacle under vacuum conditions, maintaining said separate supply paths and said combined flow path closed from the surrounding atmosphere, initiating flow of pharmaceutical liquid from one of said supply containers along one of said separate supply paths to said receptacle by opening a first closure means in said one supply path, weighing said receptacle as the pharmaceutical liquid flows along said one supply path to said receptacle, closing off said one supply path by closing said first closure means after a predetermined amount and weight of pharmaceutical liquid has passed from said one supply container to said receptacle, initiating flow of pharmaceutical liquid from another of said supply containers along another of said separate supply paths to said receptacle by opening a second closure means in said other supply path, weighing said receptacle as the pharmaceutical liquid flows along said other supply path to said receptacle, closing off said other supply path by closing said second closure means after a predetermined amount and weight of pharmaceutical liquid has passed from said other supply container to said receptacle, repeating the aforesaid steps sequentially for each one of said supply containers and associated separate flow paths, sensing the eventual emptying of said supply containers by sensing means which sense air in the respective separate supply path, closing off the respective separate supply path by the respective closure means upon sensing the presence of air to thereby prevent air from entering the supply path downstream of the respective closure means upon emptying of the respective supply container, and thereafter sealing off the contents of said receptacle, whereby the receptacle thereby receives a predetermined amount and weight of pharmaceutical liquid from each of said supply containers along a flow path closed from the surrounding atmosphere and upon eventual emptying of each supply container, air is prevented form entering said receptacle, thereby providing for automatic and exact filling of the receptacle under sterile conditions.

20. Apparatus for the automatic preparation and accurate mixing of predetermined amounts of pharmaceutical liquids contamination-free in a closed system, comprising a plurality of closed supply containers containing the liquid components to be mixed, a supply tube leading from each of said containers, a connector means having a plurality of connector inlets and a plurality of connector outlets with each of said connector inlets being connected to each of said connector outlets, each of said supply tubes being connected to one of said connector inlets of said connector means, a sensor means in each of said supply tubes located between said supply container and said connector means, said sensor means including means to sense emptying of the respective supply container by sensing air in the respective supply tube, closure means in each of said supply tubes located between said sensor means and said connector means and operable to close off the respective supply tube when said sensor means senses emptying of the respective supply container, a vacuum chamber, a plurality of receptacles to be filled with the mixed pharmaceutical liquid, one of said receptacles being disposed within said vacuum chamber, a conduit connected to each of said outlet connections of said connector means and connected to each of said receptacles, respectively, one of said conduits connected to one of said receptacles passing sealingly into said vacuum chamber, a sealing means located along said one conduit downstream of said closure means and said connector means to seal said one conduit after said one receptacle receives the pharmaceutical liquid from said supply containers, whereby the apparatus is operable to pass the liquid simultaneously from all of said closed supply containers to said one receptacle in said vacuum chamber along a sealed flow path sealed from the outside atmosphere while air is prevented from entering said one receptacle upon emptying of the respective supply container by the sensor means which operates the respective closure means to close off the respective supply tube when air is present in the respective supply tube upon emptying of the respective supply container, the apparatus thereby providing for automatic and exact filling of said one receptacle under sterile conditions, said one receptacle, upon receiving said pharmaceutical liquid and being sealed, being removed from said vacuum chamber and another of said receptacles connected to another of said conduits being placed into said vacuum chamber to receive pharmaceutical liquid from said supply containers along a flow path which is closed and which was closed when said one receptacle was receiving said pharmaceutical liquid, whereby sterile conditions are maintained during filling of said plurality of receptacles, said other receptacle being precluded from receiving pharmaceutical liquids from said supply containers during filling of said one receptacle due to the differential pressure about said one and said other receptacle during filling of said one receptacle.

21. Apparatus for the automatic preparation and accurate mixing of predetermined amounts of pharmaceutical liquids contamination-free in a closed system, comprising a plurality of closed supply containers containing the liquid components to be mixed, a supply tube leading from each of said containers, a cannula connecting each respective supply container and supply tube, a connector means having a plurality of connector inlets and a connector outlet with each of said connector inlets being in communication with said connector outlet, each of said supply tubes being connected to one of said connector inlets of said connector means, a sensor means in each of said supply tubes located between said supply container and said connector means, said sensor means including means to sense emptying of the respective supply container by sensing air in the respective supply tube, closure means in each of said supply tubes located between said sensor means and said connector means and operable to close off the respective supply tube when said sensor means senses air in the respective supply tube, a vacuum chamber, a receptacle to be filled with the mixed pharmaceutical liquid, said receptacle being disposed within said vacuum chamber, a conduit leading from said connector outlet of said connector means and passing sealingly into said vacuum chamber for connection to said receptacle, said cannulas, said supply tubes, said connector means, said conduit, and said receptacle being formed as a single connected unit which is packaged in a sterile condition, a scale means operable to weigh said receptacle, a control means connected between said scale means and said closure means and operable to selectively open and close said closure means to effect sequential flow of predetermined amounts and weights of liquid from each of said supply containers into said receptacle, and a sealing means located along said conduit downstream of said closure means of said connector means to seal said conduit after said receptacle receives said predetermined amounts and weights of pharmaceutical liquids from said supply containers, whereby the apparatus is operable to sequentially pass predetermined amounts and weights of the pharmaceutical liquids from said supply containers to said receptacle in said vacuum chamber in a flow path closed from the surrounding atmosphere, the apparatus also being operable to prevent air from entering said receptacle upon eventual emptying of the respective supply container by the sensor means which operates the respective closure means to close off the respective supply tube when air is present in the respective supply tube upon emptying of the respective supply container, the apparatus thereby providing for automatic and exact filling of receptacles under sterile conditions.

* * * * *